(12) United States Patent
Lavielle et al.

(10) Patent No.: US 6,469,011 B2
(45) Date of Patent: Oct. 22, 2002

(54) BENZENESULFONAMIDE COMPOUNDS USEFUL AS TXA2 AND 5-HT2 RECEPTOR ANTAGONISTS

(75) Inventors: Gilbert Lavielle, La Celle Saint Cloud; Bernard Cimetiere, Paris; Tony Verbeuren, Vernouillet; Serge Simonet, Conflans Sainte Honorine; Jean-Jacques Descombes, Rueil Malmaison, all of (FR)

(73) Assignee: Les Laboratoires Servier, Neuilly-Sur-Seine (FR)

( * ) Notice: Subject to any disclaimer, the term of this patent is extended or adjusted under 35 U.S.C. 154(b) by 0 days.

(21) Appl. No.: 09/764,576

(22) Filed: Jan. 18, 2001

(65) Prior Publication Data

US 2001/0009915 A1 Jul. 26, 2001

(30) Foreign Application Priority Data

Jan. 19, 2000 (FR) .............................. 00 00623

(51) Int. Cl.[7] ................... C07D 211/32; C07D 413/04; A61K 31/445; A61K 31/4965
(52) U.S. Cl. ..................... 514/255.01; 514/252.13; 514/254.04; 514/254.06; 514/255.03; 514/252.12; 514/319; 514/428; 544/359; 544/368; 544/383; 544/386; 544/403; 546/196; 546/198; 546/199; 546/205; 548/569
(58) Field of Search ............... 544/368, 359, 544/383, 403, 386; 546/205, 196, 198, 199; 514/252.13, 254.04, 254.06, 255.03, 252.12, 319, 255.01, 428; 548/569

(56) References Cited

U.S. PATENT DOCUMENTS 5,472,979 A * 12/1995 Lavielle et al. ............ 514/562

OTHER PUBLICATIONS

Dogne et al Curr. Med. Chem. 7 (2000) 609–628 (Medline abstract only).*
Gaster et al Ann. Rep. Med. Chem. 33 (1998) 21–30.*
Herman Thrombosis Research 92 (1998) S17–S21.*
Cimetiére et al Bioorg. Med. Chem. Lett. 8 (1998) 1381–1386.*
Robichaud et al Ann. Rep. Med. Chem. 35 (2000) 11–20.*

* cited by examiner

*Primary Examiner*—Deepak R Rao
(74) *Attorney, Agent, or Firm*—The Firm of Hueschen and Sage; G. Patrick Sage

(57) ABSTRACT

Compound of formula (I):

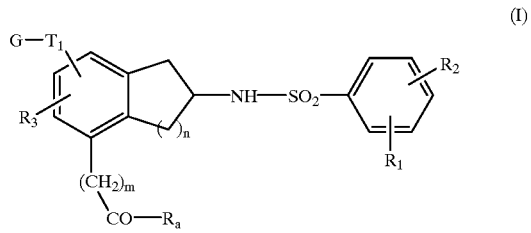

which is useful as a $TXA_2$ and $5\text{-}HT_2$ receptor antagonist and pharmaceutical compositions containing the same.

10 Claims, No Drawings

BENZENESULFONAMIDE COMPOUNDS USEFUL AS TXA2 AND 5-HT2 RECEPTOR ANTAGONISTS

DESCRIPTION OF THE PRIOR ART

Compounds having a benzenesulphonamide chain have been described in Application EP 864 561 in relation to their NO-yielding character and their thromboxane $A_2$ ($TXA_2$) receptor antagonist character, as well as in Application EP 648 741 solely in relation to their $TXA_2$ receptor antagonist properties.

The compounds of the present invention have a novel structure giving them a $TXA_2$ receptor antagonist and $5HT_2$ serotonergic receptor antagonist character.

BACKGROUND OF THE INVENTION

Platelet aggregation and vasospasms play an essential role in the etiology and development of atherothrombotic cardiovascular disorders. $TXA_2$, an arachidonic acid metabolite, and serotonin (5HT), a neurotransmitter, are both powerful vasoconstrictor agents, and are able to induce or reinforce platelet activation, resulting in the aggregation thereof. The vasoconstrictor and pro-aggregation actions of $TXA_2$ are effected through the intermediary of membrane receptors called TP receptors (Medicinal Research Reviews, 1991, 11, 5, p. 503) while those of serotonin are effected via the intermediary of $5HT_1$ or $5HT_2$ receptors (T.I.P.S., 1991, 121, p. 223). Research strategies pursued with the aim of finding agents that block the production and/or activation of $TXA_2$ have led to the development of selective TP receptor antagonists, of $TXA_2$-synthase inhibitors, or of mixed agents that exhibit both properties (Medicinal Research Reviews, ibid., T.I.P.S., 1991, 121, 158). Like $TXA_2$, serotonin acts by stimulating platelets and vascular contractions and its activity is found to be increased in atherothrombotic disorders.

The idea of compounds that oppose both the process that causes thromboxane to become active and the process that causes serotonin to become active is extremely useful for the clinician. Such products have the advantage of offering more complete protection both against the activation of platelets and against vasospasms. It will thus be possible for such products to be used in the treatment of pathologies associated with increased activity of $TXA_2$ and 5-HT especially in the treatment of atherothrombotic cardiovascular disorders, such as myocardial infarction, angina pectoris, cerebral vascular accidents, Raynaud's disease, and also asthma and bronchospasms, as well as migraine and venous disorders.

DETAILED DESCRIPTION OF THE INVENTION

The present invention relates to the compounds of formula (I):

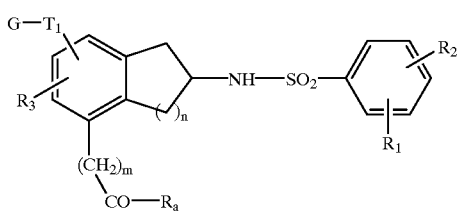

wherein:
n is an integer of from 1 to 3 inclusive,
m is an integer of from 0 to 6 inclusive,
$R_a$ represents a hydroxy, linear or branched ($C_1$–$C_6$) alkoxy, aryloxy or arylalkyloxy group,
$R_1$ and $R_2$ represent independently a hydrogen atom, a halogen atom, an alkyl group, a linear or branched ($C_1$–$C_6$)alkoxy group, a hydroxy group or a linear or branched ($C_1$–$C_6$)perhaloalkyl group,
$R_3$ represents a hydrogen atom or an alkyl, arylalkyl, cycloalkylalkyl, aryl or cycloalkyl group,
$T_1$ represents an alkylene, O-alkylene, alkylene-O— or ($C_1$–$C_3$)alkylene-O—($C_1$–$C_3$)-alkylene group,
G represents a $G_1$- or $G_1$-$T_2$-A- group wherein:
A represents an aryl group,
$T_2$ represents a bond or an alkylene, —O-alkylene, alkylene-O— or ($C_1$–$C_3$)alkylene-O—($C_1$–$C_3$) alkylene group,
$G_1$ represents a —$NR_4R_5$ group wherein $R_4$ and $R_5$ represent independently a hydrogen atom, or an alkyl, cycloalkyl, optionally substituted aryl, optionally substituted arylalkyl, cycloalkylalkyl, optionally substituted heteroaryl or optionally substituted heteroarylalkyl group, or $G_1$ represents a heterocycloalkyl group of formula

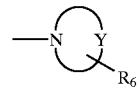

having from 5 to 7 ring members, wherein Y represents a nitrogen atom, an oxygen atom or a CH or $CH_2$ group and $R_6$ represents a hydrogen atom or an alkyl, cycloalkyl, cycloalkylalkyl, optionally substituted aryl, optionally substituted arylalkyl, optionally substituted arylcarbonyl, optionally substituted arylcarbonylalkyl, optionally substituted diarylalkyl, optionally substituted diarylalkenyl, optionally substituted (aryl)(hydroxy)alkyl, optionally substituted heteroaryl, optionally substituted heteroarylalkyl, optionally substituted heteroarylcarbonyl or optionally substituted heteroarylcarbonylalkyl group,
to their enantiomers and diastereoisomers, and also to addition salts thereof with a pharmaceutically acceptable acid or base,
wherein:
the term "alkyl" denotes a linear or branched chain having from 1 to 6 carbon atoms,
the term "alkenyl" denotes a chain having from 2 to 6 carbon atoms and containing from 1 to 3 double bonds,
the term "alkylene" denotes a linear or branched divalent group containing from 1 to 6 carbon atoms, unless specified otherwise,
the term "cycloalkyl" denotes a saturated cyclic group containing from 3 to 8 carbon atoms,
the term "aryl" denotes a phenyl or naphthyl group,
the term "heteroaryl" denotes a mono- or bi-cyclic group having from 4 to 11 ring members that is unsaturated or partially saturated and contains from 1 to 5 hetero atoms selected from nitrogen, oxygen and sulphur,
the terms "diarylalkyl" and "diarylalkenyl" denote, respectively, alkyl and alkenyl groups as defined hereinbefore, substituted by two identical or different aryl groups as defined hereinbefore,
the term "substituted" relating to aryl, arylalkyl, arylcarbonyl, arylcarbonylalkyl, diarylalkyl, diarylalkenyl, heteroaryl, heteroarylalkyl, heteroarylcarbonyl and heteroarylcarbonylalkyl denotes that the groups in question are substituted in the aromatic moiety by one or more halogen atoms, alkyl groups, linear or branched ($C_1$–$C_6$)alkoxy groups, hydroxy groups, cyano groups, nitro groups or amino groups (optionally substituted by one or two alkyl groups), wherein the heteroaryl and heteroarylalkyl groups may also be substituted by an oxo group.

Amongst the pharmaceutically acceptable acids there may be mentioned, without implying any limitation, hydrochloric, hydrobromic, sulphuric, phosphonic, acetic, trifluoroacetic, lactic, pyruvic, malonic, succinic, glutaric, fumaric, tartaric, maleic, citric, ascorbic, methanesulphonic, camphoric acid, etc.

Amongst the pharmaceutically acceptable bases there may be mentioned, without implying any limitation, sodium hydroxide, potassium hydroxide, triethylamine, tert-butylamine etc.

Preferred compounds of the invention are those wherein n is 2.

Other preferred compounds of the invention are those wherein m is 2.

An advantageous embodiment of the invention relates to compounds of formula (I) wherein $R_3$ represents a hydrogen atom.

Another advantageous embodiment of the invention relates to compounds of formula (I) wherein $R_a$ represents a hydroxy group.

In the compounds of formula (I), $G_1$ preferably represents a heterocycloalkyl group of formula

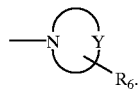

There may be mentioned, for example, without implying any limitation, the groups piperidine, pyrrole, piperazine . . .

Advantageously, in the groups $G_1$, $R_6$ represents a group selected from alkyl (for example methyl), arylcarbonyl (for example benzoyl), arylcarbonylalkyl (for example benzoylmethyl), diarylalkenyl (for example bisphenylmethylene), (aryl)(hydroxy)alkyl (for example (phenyl)(hydroxy)methyl), aryl (for example phenyl), and heteroaryl, each of those groups being optionally substituted in their aromatic moiety where such a moiety is present. Advantageously, the substituent chosen will be a halogen atom or an alkoxy group.

Amongst the preferred heteroaryl groups there may be mentioned more especially the groups 1,2-benzisoxazole, 1,2-benzisothiazole, . . .

An especially advantageous embodiment of the invention relates to compounds of formula (I) wherein n and m are each 2, $R_a$ represents a hydroxy group, $R_2$ and $R_3$ each represents a hydrogen atom, $R_1$ represents a halogen atom, and $G_1$ represents a heterocycloalkyl group of formula

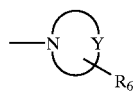

wherein Y represents a nitrogen atom or a —CH or $CH_2$ group, and $R_6$ is selected from the groups alkyl, arylcarbonyl, arylcarbonylalkyl, diarylalkenyl, (aryl)(hydroxy)alkyl, aryl and heteroaryl.

Amongst the preferred compounds of the invention there may be mentioned more especially 3-(6-{[(4-chlorophenyl)sulphonyl]amino}-3-{2-[4-(6-fluoro-1,2-benzisothiazol-3-yl)-1-piperidinyl]ethyl}-5,6,7,8-tetrahydro-1-naphthyl)propanoic acid and 3-(6-{[(4-chlorophenyl)sulphonyl]amino}-3-{[2-(4-methyl-1-piperazinyl)phenoxy]methyl}-5,6,7,8-tetrahydro-1-naphthyl)propanoic acid.

The present invention relates also to a process for the preparation of the compounds of formula (I), which process is characterised in that there is used as starting material a compound of formula (II):

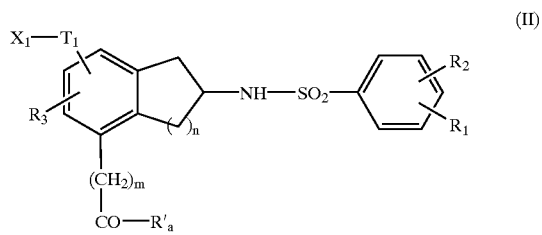

(II)

wherein n, m, $R_1$, $R_2$, $R_3$ and $T_1$ are as defined for formula (I), $R'_a$ represents a linear or branched ($C_1$–$C_6$)alkoxy group and $X_1$ represents a leaving group (for example a halogen atom or a tosyl group), which, when it is desired to obtain compounds of formula (I) wherein G represents a group $G_1$ as defined for formula (I), is treated in basic medium with a compound of formula $G_1H$ to yield a compound of formula (I/a):

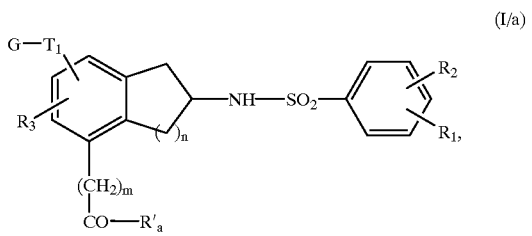

(I/a)

a particular case of the compounds of formula (I) wherein m, n, $R'_a$, $R_1$, $R_2$, $R_3$, $T_1$ and $G_1$ are as defined for formula (I), or which, when it is desired to obtain compounds of formula (I) wherein G represents a group $G_1$-$T_2$-A- as defined for formula (I), is treated in basic medium with a compound of formula HO-$T_2$-A-$G_R$, wherein $T_2$ and A are as defined for formula (I) and $G_R$ represents a reactive group so selected that it can effect nucleophilic substitution of the leaving group $X_1$ present in the substrate to yield a compound of formula (IV):

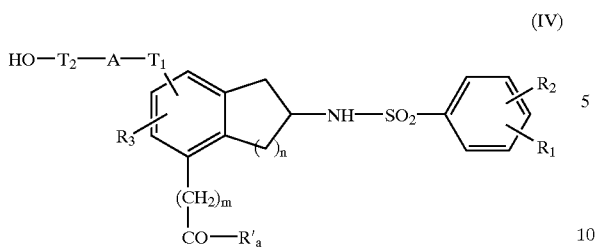

(IV)

wherein m, n, $R'_a$, $R_1$, $R_2$, $R_3$, $T_1$, A and $T_2$ are as defined hereinbefore, the hydroxy group of which is converted into a leaving group or into a halogen atom to yield a compound of formula (V):

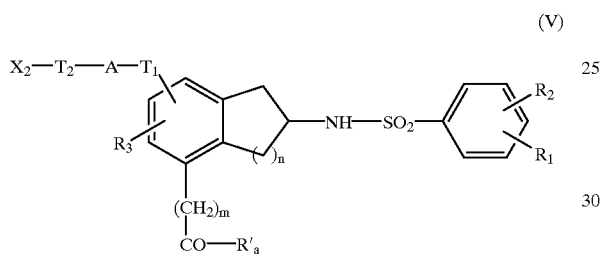

(V)

wherein m, n, $R'_a$, $R_1$, $R_2$, $R_3$, $T_1$, A and $T_2$ are as defined hereinbefore and $X_2$ represents a leaving group (for example a halogen atom or a tosyl group), which compound of formula (V) is treated in basic medium with a compound of formula $G_1H$, $G_1$ being as defined for formula (I), to yield a compound of formula (I/b):

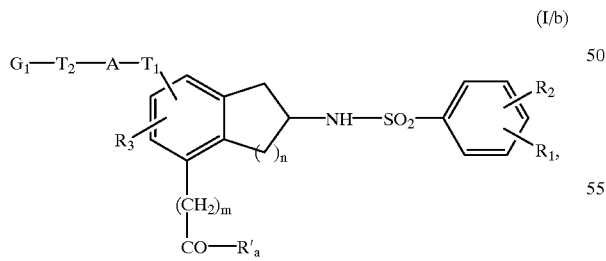

(I/b)

a particular case of the compounds of formula (I) wherein m, n, $R'_a$, $R_1$, $R_2$, $R_3$, $T_1$, $T_2$, A and $G_1$ are as defined hereinbefore, which compounds of formulae (I/a) and (I/b) may be subjected to hydrolysis of the ester function, in acid or basic medium according to the reactive groups present in the molecule, to yield a compound of formula (I/c):

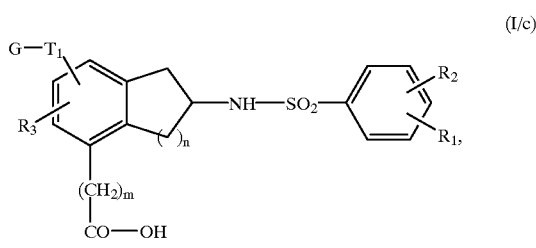

(I/c)

a particular case of the compounds of formula (I) wherein m, n, $R_1$, $R_2$, $R_3$ and $T_1$ are as defined hereinbefore and G is as defined for formula (I), which compounds (Ia), (I/b) and (I/c) constitute the totality of the compounds of formula (I), and:
may, if necessary, be purified according to a conventional purification technique,
are optionally separated into their stereoisomers according to a conventional separation technique,
are converted, if desired, into addition salts with a pharmaceutically acceptable acid or base,
wherein, at any moment considered appropriate during the course of the process described above, the carboxylic ester function —CO—$R'_a$ may be hydrolysed to the corresponding acid, which may be converted again to a different ester as required by the synthesis.

The present invention relates also to pharmaceutical compositions comprising as active ingredient one compound of formula (I), on its own or in combination with one or more pharmaceutically acceptable, inert, non-toxic excipients or carriers.

Amongst the pharmaceutical compositions according to the invention there may be mentioned more especially those which are suitable for oral, parenteral or nasal administration, tablets or dragees, sublingual tablets, gelatin capsules, lozenges, suppositories, creams, ointments, dermal gels, etc.

The useful dosage varies in accordance with the age and weight of the patient, the nature and the severity of the disorder and also the administration route, which may be oral, nasal, rectal or parenteral. Generally, the unit dosage ranges from 0.1 mg to 500 mg for a treatment of from 1 to 3 administrations per 24 hours.

The following Examples illustrate the invention and do not limit it in any way.

The starting materials employed are known products or products prepared according to known procedures.

PREPARATION A

Methyl 3-(3-(bromomethyl)-6-{[(4-chlorophenyl)sulphonyl]amino}-5,6,7,8-tetrahydro-1-naphthyl)propanoate Step a: Methyl 3-(6-{[(4-chlorophenyl)sulphonyl]amino}-3-formyl-5,6,7,8-tetrahydro-1-naphthyl)propanoate 2.5 g of a solution of osmium tetroxide (2.5% by weight) in 2-methyl-2-propanol, and then 20 g of sodium periodate, are added at ambient temperature to a solution of 10 g (23 mmol) of methyl 3-(6-{[(4-chlorophenyl)sulphonyl]amino}-3-vinyl-5,6,7,8-tetrahydro-1-naphthyl)propanoate, described in Application EP 864 561, in a mixture of 100 ml of dioxan and 50 ml of water. After stirring for one night at ambient temperature, the solution is filtered and the filtrate is concentrated. The residue obtained is taken up in dichloromethane and washed with water, and the organic phase is dried and concentrated and then purified by chromatography on silica gel, using as eluant a cyclohexane/ethyl acetate mixture (60/40), to yield the expected compound.

Step b: Methyl 3-(6-{[(4-chlorophenyl)sulphonyl] amino}-3-hydroxymethyl-5,6,7, 8-tetrahydro-1-naphthyl) propanoate 1 g (2.6 mmol) of sodium borohydride is added to a solution of 4 g (9.2 mmol) of the product described in the above Step in 100 ml of methanol. The reaction mixture is stirred for 30 minutes at ambient temperature. After the addition of a saturated aqueous solution of sodium hydrogen carbonate and evaporation of the majority of the methanol, the reaction mixture is extracted with dichloromethane. The organic phase is dried and concentrated. Purification by chromatography on silica gel, using as eluant an ethyl acetate/cyclohexane mixture (50/50), yields the expected product.

Step c: Methyl 3-(3-(bromomethyl)-6-{[(4-chlorophenyl) sulphonyl]amino}-5,6,7, 8-tetrahydro-1-naphthyl) propanoate At ambient temperature, 2.23 g (8.5 mmol) of triphenylphosphine and then, slowly, a solution of 2.83 g (8.5 mmol) of carbon tetrabromide in 25 ml of dichloromethane, are added to a solution of 3.10 g (7.1 mmol) of the product described in the above Step in 50 ml of dichloromethane. After stirring at ambient temperature for one hour, the solvent is evaporated off. Purification by chromatography on silica gel, using as eluant a cyclohexane/ethyl acetate mixture (80/20), yields the expected product.

PREPARATION B

Methyl 3-(3-(3-bromopropyl)-6-{[(4-chlorophenyl) sulphonyl]amino}-5,6,7,8-tetrahydro-1-naphthyl) propanoate Step a: Tert-butyl 3-(7-{[(4-chlorophenyl)sulphonyl] amino}-4-[2-(methoxycarbonyl)ethyl]-5,6,7,8-tetrahydro-1-naphthyl)-2-propenoate 1.25 g (4 mmol) of tri-o-tolylphosphine, 8.5 ml of triethylamine, 230 mg (1 mmol) of palladium acetate and 9 ml of tert-butyl acrylate are added to a solution of 10 g (20.5 nmol) of methyl 3-(3-bromo-6-{[(4-chlorophenyl) sulphonyl]amino}-5,6,7,8-tetrahydro-1-naphthyl) propanoate, described in Application EP 864 561, in 250 ml of DMF. The reaction mixture is stirred at 110° C. for 8 hours. The solvent is then evaporated off, and purification by chromatography on silica gel, using as eluant a cyclohexane/ethyl acetate mixture (80/20), yields the expected product.

Step b. Methyl 3-([3-(2-tert-butoxycarbonyl)ethyl]-6-{ [(4-chlorophenyl)-sulphonyl]amino}-5,6,7,8-tetrahydro-1-naphthyl)propanoate 0.87 g (3.6 mmol) of cobalt chloride hexahydrate, and then, in portions, 1.1 g (2.9 mmol) of sodium borohydride, are added to a solution of 7.5 g (14 mmol) of the product described in the above Step in 100 ml of methanol. The reaction mixture is stirred for 2 hours at ambient temperature and then filtered. The solvent is evaporated off, and the residue is purified by chromatography on silica gel, using as eluant a cyclohexane/ethyl acetate mixture (80/20), to yield the expected product.

Step c: 3-(7-{[(4-Chlorophenyl)sulphonyl]amino}-4-[2-(methoxycarbonyl)ethyl]-5,6,7,8-tetrahydro-2-naphthyl) propanoic acid A solution of 6.4 g (12 mmol) of the product described in the above Step in 50 ml of trifluoroacetic acid is stirred for 12 hours at ambient temperature. The solvent is then evaporated off and the residue is taken up in ethyl acetate. The organic phase is washed with brine and then dried and evaporated. The product is obtained after purification by chromatography on silica gel with a dichloromethane/methanol mixture (98/2) as eluant.

Step d: Methyl 3-(6-{[(4-chlorophenyl)sulphonyl] amino}-3-(3-hydroxypropyl)-5,6,7,8-tetrahydro-1-naphthyl)propanoate 9 ml of a 1M solution of $BH_3$/THF in THF are slowly added, at ambient temperature, to a solution of 2.8 g (5.2 mmol) of the product described in the above Step in 80 ml of THF. After stirring the mixture for one night at ambient temperature, 10 ml of water are added. The majority of the solvent is evaporated off, and the residue is taken up in ethyl acetate. The organic phase is then washed with brine, dried and evaporated to yield the expected product.

Step e: Methyl 3-(6-{[(4-chlorophenyl)sulphonyl] amino}-3-(3-bromopropyl)-5,6,7,8-tetrahydro-1-naphthyl) propanoate The product is obtained in accordance with the procedure described in Preparation A, Step c, using as starting material the compound described in the above Step.

PREPARATION C

Methyl 3-(6-{[(4-chlorophenyl)sulphonyl]amino}-3-({4-[2-(tosyloxy)ethyl]phenoxy}methyl)-5,6,7,8-tetrahydro-1-naphthyl)propanoate Step a: Methyl 3-(6-{[(4-chlorophenyl)sulphonyl] amino}-3-[4-(2-hydroxyethyl)phenoxymethyl]-5,6,7,8-tetrahydro-1-naphthyl)propanoate 165 mg (4.2 mmol) of sodium hydride (60% in mineral oil), and then a solution of 1.05 g (2.1 mmol) of the product described in Preparation A in 50 ml of THF and 1.11 g of crown ether $C_{18-6}$, are added to a solution of 0.58 g (4.2 mmol) of 2-(4-hydroxyphenyl)ethanol in 100 ml of THF. The reaction mixture is heated at reflux for one hour. The majority of the THF is evaporated off, and the mixture is hydrolysed, and adjusted to an acid pH using IN hydrochloric acid. After extraction with dichloromethane, drying and purification by chromatography on silica gel, using as eluant an ethyl acetate/cyclohexane mixture (50/50), the expected product is obtained.

Step b. Methyl 3-(6-{[(4-chlorophenyl)sulphonyl] amino}-3-({4-[2-(tosyloxy)ethyl]phenoxy}methyl)-5,6,7,8-tetrahydro-1-naphthyl)propanoate 1 g (5.4 mmol) of tosyl chloride, and then 0.5 ml of pyridine, are added to a solution of 0.75 g (1.35 mmol) of the product obtained in the above Step in 50 ml of dichloromethane. After stirring at ambient temperature for one night, the mixture is washed with IN hydrochloric acid and dried. After evaporation of the solvent and purification by chromatography on silica gel, using as eluant a cyclohexane/ethyl acetate mixture (60/40), the expected product is obtained.

PREPARATION D (2,3-Dimethoxy)(4-piperidinyl)methanol

Step a: 1-Benzyl-4-piperidinylcarboxamide

A mixture of 20 g (156 mmol) of isonipecotamide, 32.4 g (234 mmol) of potassium carbonate, 2 g (12 mmol) of potassium iodide and 18.6 ml (156 mmol) of benzyl bromide in 400 ml of acetonitrile is heated at reflux for 5 hours. The solvent is evaporated off and the residue is taken up in a dichloromethane/water mixture. After decanting, extracting with dichloromethane, washing the organic phases with brine and drying, removal of the solvent by evaporation yields the expected product.

Step b: 1-Benzyl-4-piperidylcarbonitrile 26 g (119 mmol) of the product described in the above Step are added in portions to a mixture of 83 ml (890 mmol) of phosphorus oxychloride and 17 g (290 mmol) of sodium chloride. The mixture is heated at reflux for one hour. After cooling, the reaction mixture is poured into 75 ml of concentrated ammonium hydroxide solution. After extraction with dichloromethane, washing the organic phase with water and drying, removal of the solvent by evaporation yields the expected product.

Step c: 1-Benzyl-4-piperidylcarbaldehyde 120 ml of a 1M solution of diisobutylaluminium hydride in hexane are added, at 0° C., to a solution of 22 g (110 mmol) of the product described in the above Step in 500 ml of THF. The mixture is stirred at ambient temperature for 2 hours. After hydrolysis with a 10% hydrochloric acid solution, the mixture is neutralised with a concentrated aqueous sodium hydroxide solution. After extraction with diethyl ether, drying, and removal of the solvent by evaporation, purification by chromatography on silica gel, using as eluant a cyclohexane/ethyl acetate mixture (50/50), yields the expected product.

Step d: (1-Benzyl-4-piperidyl)(2,3-dimethoxyphenyl)methanol 32.5 ml of a 1.6M solution of n-butyllithium in hexane are added at 0° C. to a solution of 7.07 g (51 mmol) of veratrole in 150 ml of THF. After stirring for 2 hours at 0° C., the reaction mixture is cooled to −78° C. and a solution of 8.6 g (42 mmol) of the product described in the above Step in 200 ml of THF is added. Stirring is continued for one hour at −78° C. After returning to ambient temperature, the mixture is hydrolysed with water, extracted with ethyl acetate, dried and concentrated. Purification by chromatography on silica gel, using ethyl acetate as eluant, yields the expected product.

Step e: (2,3-Dimethoxyphenyl)(4-piperidyl)methanol

A mixture of 7.5 g (22 mmol) of the product described in the above Step, 1.5 g of palladium on carbon (10%) and 5.5 g (87 mmol) of ammonium formate in 150 ml of methanol and 30 ml of water is heated at reflux for one hour. After returning to ambient temperature and filtration, the solvent is evaporated off. The residue is taken up in dichloromethane and treated with 2N sodium hydroxide solution until a pH of 10 is reached. After extraction with dichloromethane, drying and removal of the solvent by evaporation, the expected product is obtained.

PREPARATION E 2-(4-Methyl-1-piperazinyl)phenol

Step a: Ethyl 4-(2-hydroxyphenyl)-1-piperazinylcarboxylate 15 ml (156 mmol) of ethyl chloroformate are added to a solution of 18 g (100 mmol) of 2-(1-piperazinyl)phenol in 250 ml of dichloromethane. After stirring at ambient temperature for one hour, the mixture is hydrolysed and then extracted with dichloromethane. The organic phase is washed with a 1N hydrochloric acid solution and dried. Following concentration, the residue obtained is recrystallised from ether to yield the expected product.

Step b: Ethyl 4-[2-(tosyloxy)phenyl]-1-piperazinylcarboxylate 25 g (130 mmol) of para-toluenesulphonyl chloride and 20 ml of triethylamine are added at ambient temperature to a solution of 23 g (91 mmol) of the product described in the above Step in 100 ml of dichloromethane. After stirring for 72 hours at ambient temperature, the solvent is evaporated off. Chromatography on silica gel, using as eluant an ethyl acetate/cyclohexane mixture (30/70), yields the expected product.

Step c: [2-(4-Methyl-1-piperazinyl)phenol] 4-toluenesulphonate 3 g (79 mmol) of lithium aluminium hydride are added at 0° C. to a solution of 23.2 g (57 mmol) of the product described in the above Step in 100 ml of THF. The mixture is stirred for 2 hours at ambient temperature and then hydrolysed. After concentration and extraction with dichloromethane, the organic phase is dried and concentrated to yield the expected compound.

Step d: 2-(4-Methyl-1-piperazinyl)phenol

A mixture of 18 g (52 mmol) of the product described in the above Step and 44 g (785 mmol) of potassium hydroxide in 400 ml of ethanol is heated at reflux for 2 hours. After returning to ambient temperature, the pH is adjusted to 7 using 1N hydrochloric acid. Following concentration, the mixture is extracted with dichloromethane and the organic phase is dried and then concentrated to yield the expected product.

PREPARATION F 4-(4-Methyl-1-piperazinyl)phenol

The product is obtained in accordance with the procedure described in Preparation E, with the replacement of 2-(1-piperazinyl)phenol with 4-(1-piperazinyl)phenol in Step a.

EXAMPLE 1

3-(6-{[(4-Chlorophenyl)sulphonyl]amino}-3-{2-[4-(4-fluorobenzoyl)-1-piperidinyl]ethyl}-5,6,7,8-tetrahydro-1-naphthyl)propanoic acid Stade a: Methyl 3-(6-{[(4-chlorophenyl)sulphonyl]amino}-3-{2-[4-(4-fluorobenzoyl)-1-piperidinyl]ethyl}-5,6,7,8-tetrahydro-1-naphthyl)propanoate 6.5 g (17.3 mmol) of 4-(4-fluorobenzoyl)piperidine tosylate and 2.4 g (17.3 mmol) of potassium carbonate are added to a solution of 3.5 g (5.7 mmol) of methyl 3-[6-{[(4-chlorophenyl)sulphonyl]amino}-3-(2-{[(4-methylphenyl)sulphonyl]oxy}ethyl)-5,6,7,8-tetrahydro-1-naphthyl]propanoate, described in Application EP 864 561, in 100 ml of DMF. The reaction mixture is heated at reflux for one hour, then concentrated. The residue is taken up in dichloromethane and washed with water. The organic phase is dried and concentrated and then purified by chromatography on silica gel, using as eluant a dichloromethane/methanol/ammonia mixture (98/2/0.2), to yield the expected compound.

Stade b: 3-(6-{[(4-Chlorophenyl)sulphonyl]amino}-3-{2-[4-(4-fluorobenzoyl)-1-piperidinyl]ethyl}-5,6,7,8-tetrahydro-1-naphthyl)propanoic acid A solution of 2.2 g (3.5 mmol) of the product described in the above Step is heated at reflux for two hours in the presence of 3.5 ml of 2N sodium hydroxide solution. The reaction mixture is filtered and the filtrate is concentrated. 100 ml of water are added and the pH is adjusted to 5 using acetic acid. The precipitate formed is then filtered off and recrystallised from dichloromethane to yield the title compound.

Melting point: 210° C.

Elemental microanalysis:

|  | C % | H % | N % | S % |
|---|---|---|---|---|
| Calculated: | 63.20 | 5.79 | 4.47 | 5.11 |
| Found: | 62.89 | 5.87 | 4.46 | 4.82 |

EXAMPLE 2

3-[6-{[(4-Chlorophenyl)sulphonyl]amino}-3-(2-{4-[(2,3-dimethoxyphenyl)(hydroxy)methyl]-1-piperidinyl}ethyl)-5,6,7,8-tetrahydro-1-naphthyl]propanoic acid The expected product is obtained in accordance with the procedure described in Example 1, with the replacement in Step a of 4-(4-fluorobenzoyl)piperidine tosylate with the compound described in Preparation D.

Elemental microanalysis:

|  | C % | H % | N % | S % |
|---|---|---|---|---|
| Calculated: | 62.63 | 6.46 | 4.17 | 4.78 |
| Found: | 62.13 | 7.00 | 4.17 | 4.64 |

EXAMPLE 3

3-(6-{[(4-Chlorophenyl)sulphonyl]amino}-3-{2-[4-(6-fluoro-1,2-benzisoxazol-3-yl)-1-piperidinyl]ethyl}-5,6,7,8-tetrahydro-1-naphthyl)propanoic acid The expected product is obtained in accordance with the procedure described in Example 1, with the replacement of 4-(4-fluorobenzoyl)piperidine tosylate with 6-fluoro-3-piperidin-4-ylbenzo[d]isoxazole hydrochloride in Step a.

Melting point: 125° C.

Elemental microanalysis:

|  | C % | H % | N % | S % |
|---|---|---|---|---|
| Calculated: | 61.92 | 5.51 | 6.56 | 5.01 |
| Found: | 61.33 | 5.45 | 6.36 | 4.91 |

EXAMPLE 4

3-(6-{[(4-Chlorophenyl)sulphonyl]amino}-3-{2-[4-(6-fluoro-1,2-benzisothiazol-3-yl)-1-piperidinyl]ethyl}-5,6,7,8-tetrahydro-1-naphthyl)propanoic acid The expected product is obtained in accordance with the procedure described in Example 1, with the replacement of 4-(4-fluorobenzoyl)piperidine tosylate with 6-fluoro-3-piperidin-4-ylbenzo[d]isothiazole hydrochloride in Step a.

Melting point: 232° C.

Elemental microanalysis:

|  | C % | H % | N % | S % |
|---|---|---|---|---|
| Calculated: | 60.40 | 5.38 | 6.40 | 9.77 |
| Found: | 60.17 | 5.36 | 6.39 | 9.50 |

EXAMPLE 5

3-(6-{[(4-Chlorophenyl)sulphonyl]amino}-3-{2-[4-(1,2-benzisothiazol-3-yl)-1-piperazinyl]ethyl}-5,6,7,8-tetrahydro-1-naphthyl)propanoic acid The expected product is obtained in accordance with the procedure described in Example 1, with the replacement of 4-(4-fluorobenzoyl)piperidine tosylate with 3-piperazin-1-ylbenzo[d]isothiazole hydrochloride in Step a.

EXAMPLE 6

3-(3-(2-{4-[bis(4-Fluorophenyl)methylene]-1-piperidinyl}ethyl)-6-{[(4-chlorophenyl)sulphonyl]amino}-5,6,7,8-tetrahydro-1-naphthyl)-propanoic acid The expected product is obtained in accordance with the procedure described in Example 1, with the replacement of 4-(4-fluorobenzoyl)piperidine tosylate with bis(4-fluorophenyl)methylenepiperidine in Step a.

Melting point: 242° C.

Elemental microanalysis:

|  | C % | H % | N % | S % |
|---|---|---|---|---|
| Calculated: | 66.42 | 5.57 | 3.97 | 4.55 |
| Found: | 66.27 | 5.52 | 4.05 | 4.32 |

EXAMPLE 7

3-[6-{[(4-Chlorophenyl)sulphonyl]amino}-3-(2-{3-[2-(4-fluorophenyl)-2-oxoethyl]-1-pyrrolidinyl}ethyl)-5,6,7,8-tetrahydro-1-naphthyl)propanoic acid The expected product is obtained in accordance with the procedure described in Example 1, with the replacement of 4-(4-fluorobenzoyl)piperidine tosylate with 1-(4-fluorophenyl)-2-pyrrolidin-3-ylethanone hydrochloride in Step a.

Melting point: 143° C.

Elemental microanalysis:

|  | C % | H % | N % | S % |
|---|---|---|---|---|
| Calculated: | 63.20 | 5.79 | 4.47 | 5.11 |
| Found: | 63.79 | 5.79 | 4.52 | 4.99 |

EXAMPLE 8

3-(6-{[(4-Chlorophenyl)sulphonyl]amino}-2-{2-[4-(4-fluorobenzoyl)-1-piperidinyl]ethyl}-5,6,7,8-tetrahydro-1-naphthyl)propanoic acid The expected product is obtained in accordance with the procedure described in Example 1, with the replacement of methyl 3-[6-{[(4-chlorophenyl)sulphonyl]amino}-3-(2-{[(4-methylphenyl)sulphonyl]oxy}ethyl)-5,6,7,8-tetrahydro-1-naphthyl]propanoate with methyl 3-[6-{[(4-chlorophenyl)sulphonyl]amino}-2-(2-{[(4-methylphenyl)sulphonyl]oxy}ethyl)-5,6,7,8-tetrahydro-1-naphthyl]propanoate described in Application EP 864 561.

Melting point: 223° C.

Elemental microanalysis:

|  | C % | H % | N % | S % |
|---|---|---|---|---|
| Calculated: | 63.20 | 5.79 | 4.47 | 5.11 |
| Found: | 63.14 | 5.80 | 4.56 | 5.17 |

EXAMPLE 9

3-(6-{[(4-Chlorophenyl)sulphonyl]amino}-3-{[4-(4-fluorobenzoyl)-1-piperidinyl]methyl}-5,6,7,8-tetrahydro-1-naphthyl)propanoic acid The expected product is obtained in accordance with the procedure described in Example 1, with the replacement of methyl 3-[6-{[(4-chlorophenyl)sulphonyl]amino}-3-(2-{[(4-methylphenyl)sulphonyl]oxy}ethyl)-5,6,7,8-tetrahydro-1-naphthyl]propanoate with the product described in Preparation A.

Melting point: 147° C.

Elemental microanalysis:

|  | C % | H % | N % | S % |
|---|---|---|---|---|
| Calculated: | 62.69 | 5.59 | 4.59 | 5.23 |
| Found: | 62.99 | 5.49 | 4.48 | 5.17 |

EXAMPLE 10

3-(6-{[(4-Chlorophenyl)sulphonyl]amino}-3-{3-[4-(4-fluorobenzoyl)-1-piperidinyl]propyl}-5,6,7,8-tetrahydro-1-naphthyl)propanoic acid The expected product is obtained in accordance with the procedure described in Example 1, with the replacement of methyl 3-[6-{[(4-chlorophenyl)sulphonyl]amino}-3-(2-{[(4-methylphenyl)sulphonyl]oxy}ethyl)-5,6,7,8-tetrahydro-1-naphthyl]propanoate with the product described in Preparation B.

Melting point: 118° C.

Elemental microanalysis:

|  | C % | H % | N % | S % |
|---|---|---|---|---|
| Calculated: | 63.69 | 5.97 | 4.37 | 5.00 |
| Found: | 63.55 | 6.02 | 4.37 | 4.98 |

EXAMPLE 11

3-(6-{[(4-Chlorophenyl)sulphony]amino}-3-{3-[4-(4-fluorobenzoyl)-1-piperazinyl]propyl}-5,6,7,8-tetrahydro-1-naphthyl)propanoic acid The expected product is obtained in accordance with the procedure described in Example 1, with the replacement of methyl 3-[6-{[(4-chlorophenyl)sulphonyl]amino}-3-(2-{[(4-methylphenyl)sulphonyl]oxy}ethyl)-5,6,7,8-tetrahydro-1-naphthyl]propanoate with the product described in Preparation B, and of 4-(4-fluorobenzoyl)piperidine tosylate with (4-fluorophenyl)piperazine.

Elemental microanalysis:

|  | C % | H % | N % |
|---|---|---|---|
| Calculated: | 59.07 | 5.89 | 6.46 |
| Found: | 59.10 | 5.83 | 6.34 |

EXAMPLE 12

3-{6-{[(4-Chlorophenyl)sulphonyl]amino}-3-[(4-{2-[4-(4-fluorobenzoyl)-1-piperidinyl]ethyl}phenoxy)methyl]-5,6,7,8-tetrahydro-1-naphthyl}propanoic acid The expected product is obtained in accordance with the procedure described in Example 1, with the replacement of methyl 3-[6-{[(4-chlorophenyl)sulphonyl]amino}-3-(2-{[(4-methylphenyl)sulphonyl]oxy}ethyl)-5,6,7,8-tetrahydro-1-naphthyl]propanoate with the product described in Preparation C.

Melting point: 196° C.

Elemental microanalysis:

|  | C % | H % | N % | S % |
|---|---|---|---|---|
| Calculated: | 62.52 | 5.77 | 3.82 | 4.37 |
| Found: | 64.89 | 6.29 | 3.84 | 4.34 |

EXAMPLE 13

3-(6-{[(4-Chlorophenyl)sulphonyl]amino}-3-{[2-(4-methyl-1-piperazinyl)phenoxy]methyl}-5,6,7,8-tetrahydro-1-naphthyl)propanoic acid Stade a: Methyl 3-(6-{[(4-chlorophenyl)sulphonyl]amino}-3-{[2-(4-methyl-1-piperazinyl)phenoxy]methyl}-5,6,7,8-tetrahydro-1-naphthyl)propanoate A mixture of 1.30 g (2.6 mmol) of the product described in Preparation A, 0.5 g (2.6 mmol) of the product described in Preparation E, 200 mg (5.2 mmol) of sodium hydride (60% in oil) and 670 mg of crown ether $C_{18-6}$ is heated at reflux for two hours. After cooling the mixture, 2 ml of acetic acid are added and the reaction mixture is concentrated. The residue is taken up in dichloromethane and washed with water. The organic phase is dried, concentrated and purified by chromatography on silica gel, using as eluant a dichloromethane/methanol/ammonia mixture (95/5/0.5), to yield the expected product.

Stade b: 3-(6-{[(4-Chlorophenyl)sulphonyl]amino}-3-{[2-(4-methyl-1-piperazinyl)phenoxy]methyl}-5,6,7,8-tetrahydro-1-naphthyl)propanoic acid The expected product is obtained in accordance with the procedure described in Step b of Example 1, using as starting material the compound described in the above Step.

Melting point: 122° C.

Elemental microanalysis:

|  | C % | H % | N % | S % |
|---|---|---|---|---|
| Calculated: | 62.25 | 6.07 | 7.02 | 5.36 |
| Found: | 61.52 | 6.09 | 6.84 | 5.22 |

EXAMPLE 14

3-(6-{[(4-Chlorophenyl)sulphonyl]amino}-3-{[4-(4-methyl-1-piperazinyl)phenoxy]methyl}-5,6,7,8-tetrahydro-1-naphthyl)propanoic acid The expected product is obtained in accordance with the procedure described in Example 13, with the replacement in Step a of the product described in Preparation E with the product described in Preparation F.

Melting point: 148° C.

Elemental microanalysis:

|  | C % | H % | N % | S % |
|---|---|---|---|---|
| Calculated: | 62.25 | 6.07 | 7.02 | 5.36 |
| Found: | 61.94 | 6.36 | 6.66 | 5.11 |

EXAMPLE 15

3-(6-{[(4-Chlorophenyl)sulphonyl]amino}-3-{2-[4-(6-fluoro-1,2-benzo[b]thiophen-3-yl)-1-piperidinyl]ethyl}-5,6,7,8-tetrahydro-1-naphthyl)propanoic acid The expected product is obtained in accordance with the procedure described in Example 1, with the replacement of 4-(4-fluorobenzoyl)piperidine tosylate with 4-(6-fluorobenzo[b]thiophen-3-yl)piperidine hydrochloride in Step a.

Melting point: 140° C.

Elemental microanalysis:

|  | C % | H % | N % | S % |
|---|---|---|---|---|
| Calculated: | 62.32 | 5.54 | 4.28 | 9.79 |
| Found: | 62.01 | 5.36 | 4.28 | 9.80 |

EXAMPLE 16

3-(6-{[(4-Chlorophenyl)sulphonyl]amino}-3-{2-[4-(6-fluoro-1H-indazol-3-yl)-1-piperidinyl]ethyl}-5,6,7,8-tetrahydro-1-naphthyl)propanoic acid The expected product is obtained in accordance with the procedure described in Example 1, with the replacement of 4-(4-fluorobenzoyl)piperidine tosylate with 6-fluoro-3-piperidin-4-yl-1H-indazole dihydrochloride in Step a.

Melting point: 142° C.

Elemental microanalysis:

|  | C % | H % | N % | S % |
|---|---|---|---|---|
| Calculated: | 62.01 | 5.68 | 8.77 | 5.02 |
| Found: | 61.98 | 5.74 | 8.70 | 4.83 |

PHARMACOLOGICAL STUDY

EXAMPLE A

Platelet Aggregation in Man

Venous blood is obtained from human volunteers who have not taken aspirin for at least 14 days prior to the experiment. The blood is removed over sodium citrate (0.109 M) (1 vol. of citrate over 9 vol. of blood). Platelet-rich plasma (PRP) is obtained by centrifugation (20° C.) at 200 g for 10 minutes. The number of platelets is on average 250000 PL/mm$^3$. The PRP is stored at room temperature until the test and is used within 2 hours of having been taken. The $TXA_2$ agonist U46619 is used at a concentration of 1 $\mu$M and 5-hydroxytryptamine is used at a concentration of 10 $\mu$M, the latter in the presence of 0.3 $\mu$M adenosine diphosphate and 1 $\mu$M adrenalin.

The compounds of the invention inhibit platelet aggregation induced by the $TXA_2$ agonist as well as that produced by 5-hydroxytryptamine. By way of example, the $IC_{50}$ values of the compound of Example 4 are 170 nM and 230 nM respectively for the two targets. The values indicate that the compounds of the invention are powerful platelet anti-aggregants, which act in a balanced manner on the two activation routes, that of $TXA_2$ and that of serotonin.

EXAMPLE B

Pharmaceutical Composition

Formulation for the preparation of 1000 tablets each comprising 5 mg of active ingredient:

| compound of Example 4 | 5 g |
|---|---|
| hydroxypropyl methylcellulose | 2 g |
| wheat starch | 10 g |
| lactose | 100 g |
| magnesium stearate | 3 g |

We claim:

1. A compound selected from those of formula (I):

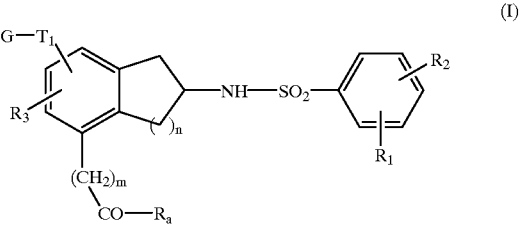

wherein:

n is 1 to 3 inclusive, m is 0 to 6 inclusive, $R_a$ represents hydroxy, linear or branched ($C_1$–$C_6$)alkoxy, aryloxy or arylalkyloxy, $R_1$ and $R_2$ represent independently hydrogen, halogen, alkyl, linear or branched ($C_1$–$C_6$)alkoxy, hydroxy or linear or branched ($C_1$–$C_6$)perhaloalkyl, $R_3$ represents hydrogen, alkyl, arylalkyl, cycloalkylalkyl, aryl or cycloalkyl, $T_1$ represents alkylene, O-alkylene, alkylene-O— or ($C_1$–$C_3$)alkylene-O—($C_1$–$C_3$)alkylene, G represents $G_1$ or $G_1$-$T_2$-A-wherein:

A represents aryl, $T_2$ represents a bond or alkylene, -O-alkylene, alkylene-O- or ($C_1$–$C_3$)alkylene-O-($C_1$–$C_3$)alkylene, $G_1$ represents a heterocycloalkyl of the formula

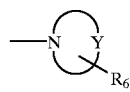

having from 5 to 7 ring members, wherein Y represents nitrogen or $CH_2$ and $R_6$ represents hydrogen, alkyl, cycloalkyl, cycloalkylalkyl, optionally substituted aryl, optionally substituted arylalkyl, optionally substituted arylcarbonyl, optionally substituted arylcarbonylalkyl, optionally substituted diarylalkyl, optionally substituted diarylalkenyl, optionally substituted (aryl)(hydroxy)alkyl, optionally substituted heteroaryl, optionally substituted heteroarylalkyl, optionally substituted heteroarylcarbonyl or optionally substituted heteroarylcarbonylalkyl, its enantiomers and diastereoisomers, and its addition salts thereof with a pharmaceutically-acceptable acid or base, wherein:

"alkyl" is a linear or branched chain having 1 to 6 carbon atoms,

"alkenyl" is a chain having 2 to 6 carbon atoms and 1 to 3 double bonds,

"alkylene" is a linear or branched divalent group consisting of 1 to 6 carbon atoms, unless specified otherwise, "cycloalkyl" is a saturated cyclic group consisting of 3 to 8 carbon atoms, "aryl" is phenyl or naphthyl, "heteroaryl" is a mono- or bi-cyclic group having 4 to 11 ring members, that is unsaturated or partially saturated and consisting of 1 to 5 hetero atoms selected from nitrogen, oxygen and sulphur, "diarylalkyl" and "diarylalkenyl" are, respectively, alkyl and alkenyl groups as defined hereinbefore, substituted by two identical or different aryl groups as defined hereinbefore, "substituted" as is relates to aryl, arylalkyl, arylcarbonyl, arylcarbonylalkyl, diarylalkyl, diarylalkenyl, heteroaryl, heteroarylalkyl, heteroarylcarbonyl and heteroarylcarbonylalkyl denotes that the groups in question are substituted in the aromatic moiety by one or more halogen atoms, alkyl groups, linear or branched ($C_1$–$C_6$)alkoxy groups, hydroxy groups, cyano groups, nitro groups or amino groups (optionally substituted by one or two alkyl groups), wherein the heteroaryl and heteroarylalkyl groups may also be substituted by an oxo group.

2. A compound of claim 1, wherein n is 2.

3. A compound of claim 1, wherein m is 2.

4. A compound of claim 1, wherein $R_3$ represents hydrogen.

5. A compound of claim 1, wherein $R_a$ represents a hydroxy group.

6. A compound of claim 1, wherein n and m are each 2, $R_a$ represents hydroxy, $R_2$ and $R_3$ each represent hydrogen, and $R_1$ represents halogen.

7. A compound of claim 1 that is 3-(6-{[(4-chlorophenyl)sulphonyl]amino}-3-{2[(4(6fluoro-1,2-benzisothiazol-3-yl)-1-piperidinyl]ethyl}-5,6,7,8-tetrahydro-1-naphthyl) propanoic acid.

8. A compound which is 3-(6-{[(4-chlorophenyl)sulphonyl]amino}-3-{[2-(4-methyl-1-piperazinyl)phenoxy]methyl}-5,6,7,8-tetrahydro-1-naphthyl) propanoic acid.

9. A method for treating an animal or human living body afflicted with a disease requiring a $TXA_2$ receptor antagonist and a 5-$HT_2$ receptor antagonist, selected from the group consisting of atherothrombotic cardiovascular disorders, Raynaud's disease, asthma, bronchospasms, migraine, and venous disorders, comprising the step of administering to the living body an amount of a compound of claim 1 which is effective for alleviation of the disease.

10. A pharmaceutical composition useful for treating an animal or human living body afflicted with a disease requiring a $TXA_2$ receptor antagonist and a 5-$HT_2$receptor antagonist, selected from the group consisting of atherothrombotic cardiovascular disorders, Raynaud's disease, asthma, bronchospasms, migraine, and venous disorders, comprising as active principle an effective amount of a compound of claim 1 together with one or more pharmaceutically-acceptable excipients or vehicle.

* * * * *

UNITED STATES PATENT AND TRADEMARK OFFICE
CERTIFICATE OF CORRECTION

| | | |
|---|---|---|
| PATENT NO. | : 6,469,011 B2 | |
| DATED | : October 22, 2002 | |
| INVENTOR(S) | : Gilbert Lavielle et al. | |

It is certified that error appears in the above-identified patent and that said Letters Patent is hereby corrected as shown below:

<u>Column 18</u>,
Line 24, "sulphonyl]amino}-3-{2[(4(6fluoro-1," should read
-- sulphonyl]amino}-3-{2-[4-(6-fluoro-1, --.

Signed and Sealed this

Thirty-first Day of August, 2004

JON W. DUDAS
*Director of the United States Patent and Trademark Office*